(12) United States Patent
Tanabe et al.

(10) Patent No.: US 8,638,361 B2
(45) Date of Patent: Jan. 28, 2014

(54) ENDOSCOPE APPARATUS

(71) Applicant: Olympus Medical Systems Corp.,
Tokyo (JP)

(72) Inventors: Takahiro Tanabe, Tachikawa (JP);
Susumu Kawata, Hachioji (JP)

(73) Assignee: Olympus Medical Systems Corp.,
Tokyo (JP)

( * ) Notice: Subject to any disclaimer, the term of this patent is extended or adjusted under 35 U.S.C. 154(b) by 0 days.

(21) Appl. No.: 13/706,918

(22) Filed: Dec. 6, 2012

(65) Prior Publication Data

US 2013/0169773 A1    Jul. 4, 2013

Related U.S. Application Data

(63) Continuation of application No. PCT/JP2012/059341, filed on Apr. 5, 2012.

(30) Foreign Application Priority Data

Apr. 18, 2011    (JP) ................................ 2011-092270

(51) Int. Cl.
*A61B 1/00* (2006.01)
*H04L 25/49* (2006.01)
*H04L 25/32* (2006.01)

(52) U.S. Cl.
USPC ............................... 348/65; 380/43; 714/798

(58) Field of Classification Search
USPC ......................................................... 361/246
See application file for complete search history.

(56) References Cited

U.S. PATENT DOCUMENTS

| 5,022,051 | A | * | 6/1991 | Crandall et al. ............... 375/292 |
| 5,438,621 | A | * | 8/1995 | Hornak et al. .................. 380/43 |
| 5,740,186 | A | * | 4/1998 | Widmer ........................ 714/753 |
| 5,841,491 | A | * | 11/1998 | D Alfonso et al. .............. 348/65 |
| 7,184,501 | B1 | * | 2/2007 | Fukuda ......................... 375/354 |
| 7,453,490 | B2 | * | 11/2008 | Gunday .......................... 348/68 |
| 2002/0131517 | A1 | * | 9/2002 | Kahlman et al. ............. 375/286 |
| 2009/0034848 | A1 | * | 2/2009 | Sakamoto et al. ............ 382/195 |

FOREIGN PATENT DOCUMENTS

| EP | 0 367 093 A2 | 5/1990 | |
| JP | 02-172327 | 7/1990 | |
| JP | 8-213969 A | 8/1996 | |
| JP | 2009-111497 | * 3/2009 | ............. H04L 25/49 |
| JP | 2009-111497 | 5/2009 | |
| WO | WO 2011/004838 A1 | 1/2011 | |

OTHER PUBLICATIONS

International Search Report dated May 22, 2012 issued in PCT/JP2012/059341.

* cited by examiner

*Primary Examiner* — Jay Patel
*Assistant Examiner* — Reza Aghevli
(74) *Attorney, Agent, or Firm* — Scully, Scott, Murphy & Presser, P.C.

(57) ABSTRACT

An endoscope apparatus has a transmission device of an endoscope and a reception device of a processor. The transmission device calculates a DC balance value of input data, compares the DC balance value and a cumulative value thereof, and compares the sign of the DC balance value and the sign of the cumulative value. When the signs are the same sign, the transmission device generates intermediate data by exchanging a first value and a second value with each other for all the bits of the input data, and generates predetermined information indicating that all the bits have been inverted. When the signs are different signs, the transmission device performs a process of setting the input data as the intermediate data and transmits the intermediate data by a serial signal.

4 Claims, 8 Drawing Sheets

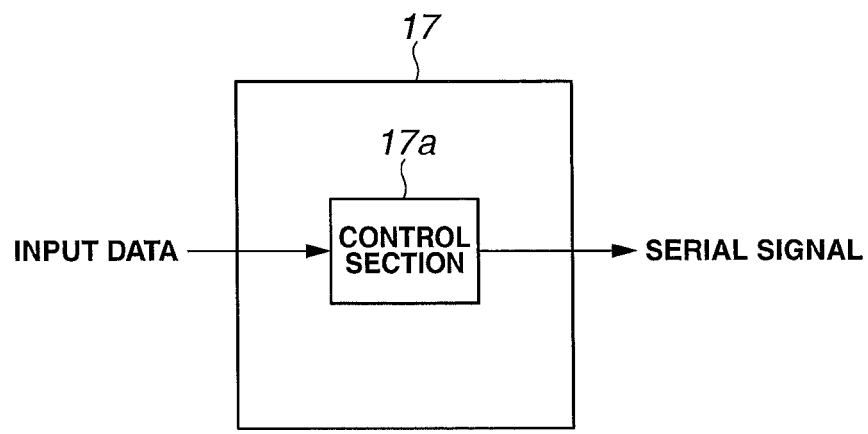
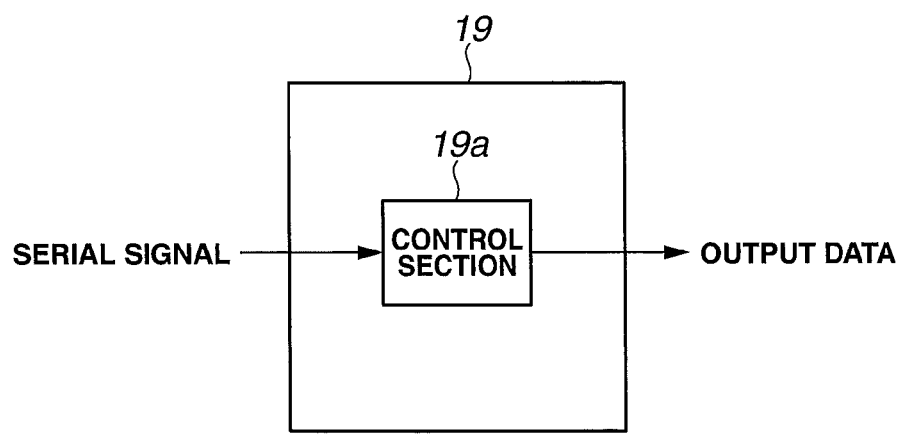

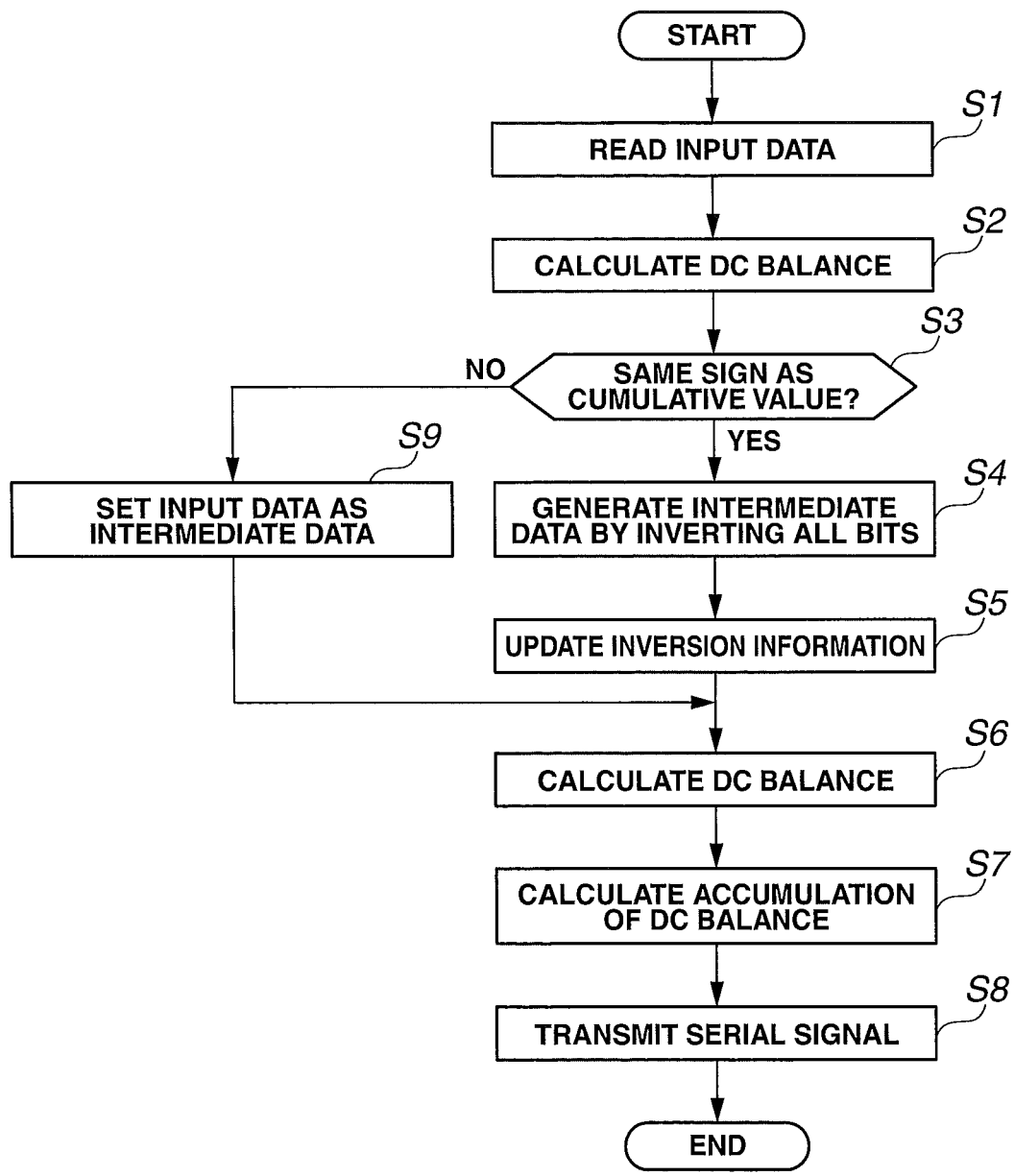

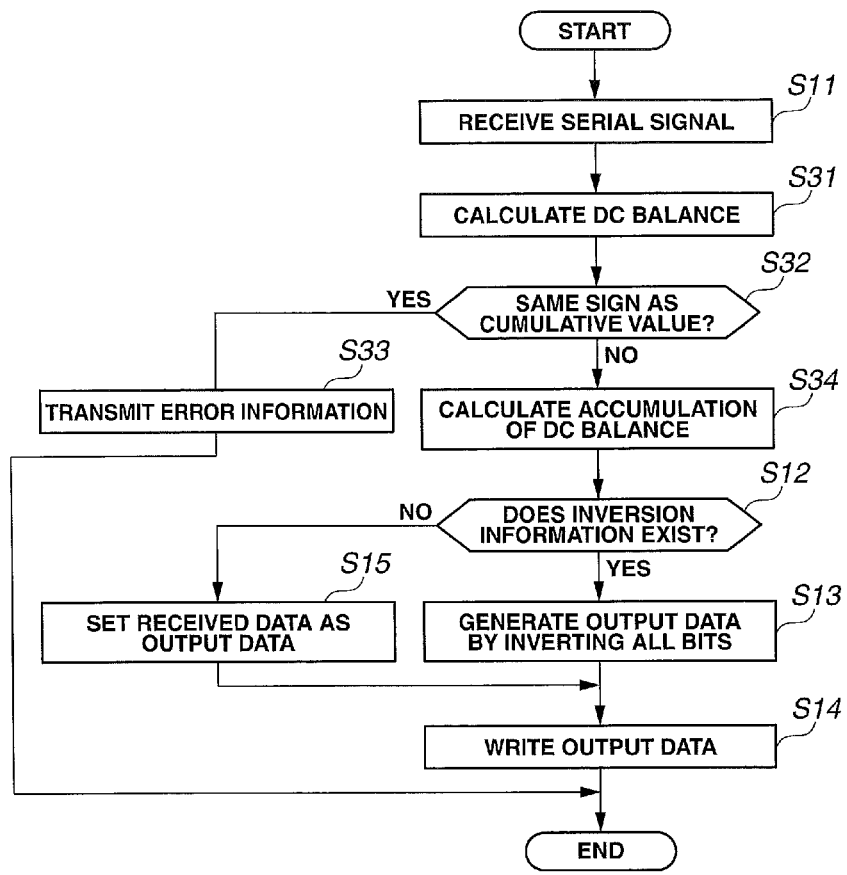
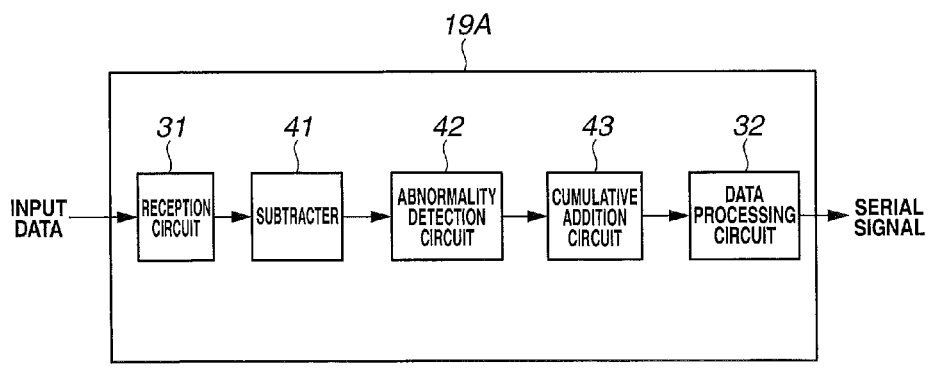

ENDOSCOPE APPARATUS

CROSS REFERENCE TO RELATED APPLICATION

This application is a continuation application of PCT/JP2012/059341 filed on Apr. 5, 2012 and claims benefit of Japanese Application No. 2011-092270 filed in Japan on Apr. 18, 2011, the entire contents of which are incorporated herein by this reference.

BACKGROUND OF THE INVENTION

1. Field of the Invention

The present invention relates to an endoscope apparatus, and in particular to an endoscope apparatus using a communication device capable of performing communication for which DC balance is ensured.

2. Description of the Related Art

Conventionally, an endoscope apparatus has been widely used in a medical field and an industrial field. The endoscope apparatus makes it possible to perform observation, image recording and the like of an endoscopy object site by inserting an endoscope insertion portion of the endoscope apparatus into a body cavity of a patient or an inside of an endoscopy object.

The endoscope apparatus is configured such that it includes the endoscope insertion portion, a processor and a monitor. Image data of an object obtained by picking up an image by an image pickup device provided at a distal end portion of the endoscope insertion portion is transmitted from the endoscope insertion portion to the processor. The processor performs image processing of received image data, generates an endoscopic image and displays the endoscopic image on the monitor. Therefore, an endoscope has an image data transmission device, and the processor has an image data reception device.

In the endoscope apparatus, a signal transmitted from the endoscope is transmitted to the processor via an insulating circuit from the viewpoint of electrical safety. However, since a DC component of the transmitted signal is blocked, it is necessary to ensure DC balance.

For example, as disclosed in Japanese Patent Application Laid-Open Publication No. 2009-111497, code conversion methods, such as the so-called Manchester encoding method and 8B 10B, have been conventionally used as a method for ensuring DC balance.

SUMMARY OF THE INVENTION

An endoscope apparatus of an aspect of the present invention is an endoscope apparatus provided with an endoscope including an image pickup device and a transmission device, and a processor including a reception device communicating with the transmission device. The transmission device of the endoscope is provided with: a first subtraction section calculating a first subtraction value obtained by subtracting a number of bits having a second value from a number of bits having a first value in input data constituted by a collection of a predetermined number of bits each of which has the first or the second value; a first data processing section performing a first predetermined process for the input data to generate intermediate data constituted by the predetermined number of bits; a second subtraction section calculating a second subtraction value obtained by subtracting the number of bits having the second value from the number of bits having the first value in the intermediate data; a first accumulation section calculating a cumulative value of the second subtraction value; and a transmission section transmitting the intermediate data by a serial signal; wherein the first predetermined process is a process of: comparing a sign of the first subtraction value of the input data and a sign of the cumulative value of the first accumulation section; generating the intermediate data by exchanging the first value and the second value with each other for all the bits of the input data and generating predetermined information indicating inversion of all the bits when the sign of the first subtraction value and the sign of the cumulative value are the same sign; and setting the input data as the intermediate data when the sign of the first subtraction value and the sign of the cumulative value are different signs. The reception device of the processor is provided with: a serial reception section receiving the serial signal and outputting the serial signal as received data for each predetermined number of bits; a second data processing section generating, for the received data, output data by exchanging the first value and the second value with each other for all the bits of the received data when the predetermined information is generated, and generating the received data which is received as the output data when the predetermined information is not generated; a third subtraction section calculating a third subtraction value obtained by subtracting the number of bits having the second value from the number of bits having the first value in the received data; a second accumulation section calculating a cumulative value of the third subtraction value; and an abnormality detection section comparing a sign of the third subtraction value of the received data and a sign of the cumulative value of the second accumulation section, and, when the sign of the third subtraction value and the sign of the cumulative value of the second accumulation section are the same sign, generating predetermined error information.

BRIEF DESCRIPTION OF THE DRAWINGS

FIG. 2 is a block diagram showing a configuration of a transmission device 17 according to the first embodiment of the present invention;

FIG. 3 is a block diagram showing a configuration of a reception device 19 according to the first embodiment of the present invention;

FIG. 4 is a flowchart showing an example of the content of a process by a control section 17a of the transmission device 17 according to the first embodiment of the present invention;

FIG. 9 is a flowchart showing an example of the content of a process by a control section 19a of a reception device 19A according to a second embodiment of the present invention;

FIG. 10 is a block diagram showing a configuration of a hardware circuit of the reception device 19A according to the second embodiment of the present invention;

DETAILED DESCRIPTION OF THE PREFERRED EMBODIMENTS

Embodiments of the present invention will be described below with reference to drawings.

First Embodiment

Figure 1:
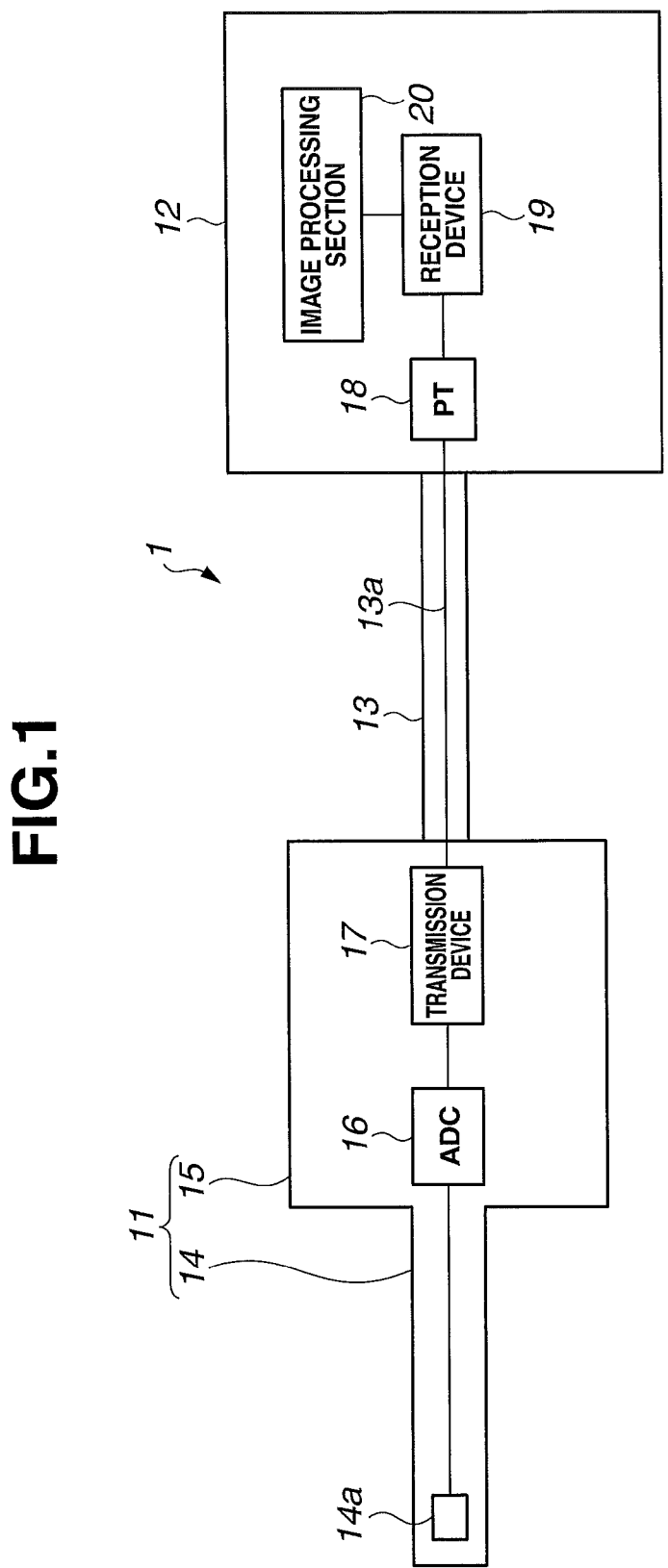
FIG. 1 is a configuration diagram showing a configuration of an endoscope apparatus according to a first embodiment of the present invention.

FIG. 1 is a configuration diagram showing a configuration of an endoscope apparatus according to the present embodiment. An endoscope apparatus 1 is configured such that it includes an endoscope 11, a processor 12, and a cable 13 connecting both of them. The endoscope 11 includes an elongated insertion portion 14 and an operation section 15, and an image pickup device 14a, such as a CCD, is provided at the distal end portion of the insertion portion 14. The operation section 15 is provided with an analog-digital converter (hereinafter referred to as an ADC) 16 and a transmission device 17. The processor 12 is provided with an insulating portion (PT) 18, a reception device 19 and an image processing section 20. The insulating portion 18 is a pulse transformer (PT). Thus, the endoscope apparatus 1 is configured such that it includes the endoscope 11 having the transmission device 17 and the processor 12 having the reception device 19. A communication device is configured with the transmission device 17 and the reception device 19 which communicates with the transmission device 17.

An image signal, which is a video signal from the image pickup device 14a, is converted to a digital signal at the ADC 16 and provided to the transmission device 17 as input data. The transmission device 17 and the insulating portion 18 are connected via multiple signal lines 13a in the cable 13. The signal outputted from the transmission device 17 is provided to the reception device 19 via the signal lines 13a having the insulating portion 18. The reception device 19 extracts image data from the received signal and provides the image data to the image processing section 20. A monitor not shown is connected to the processor 12, and an endoscopic image based on an image signal from the image processing section 20 is displayed on the monitor.

Note that only components involved in transmission and reception are shown in FIG. 1, and other components for operation signals from the operation section 15, control signals from a light source apparatus (not shown) and the like are omitted.

Next, configurations of the transmission device 17 of the endoscope 11 and the reception device 19 of the processor 12 will be described with the use of FIGS. 2 and 3. FIG. 2 is a block diagram showing the configuration of the transmission device 17. The transmission device 17 includes a control section 17a which includes a central processing unit (hereinafter referred to as a CPU), and the functions of the transmission device 17 are realized by processing by a software program executed by the control section 17a. The transmission device 17 inputs input data and transmits intermediate data by a serial signal. FIG. 3 is a block diagram showing the configuration of the reception device 19. The reception device 19 includes a control section 19a which includes a CPU, and the functions of the reception device 19 are realized by processing by a software program executed by the control section 19a. The reception device 19 obtains output data which is the same as the input data inputted to the transmission device 17, from the received serial signal. Note that the CPUs of the respective control sections 17a and 19a of the transmission device 17 and the reception device 19 may be realized, for example, by field programmable gate arrays (hereinafter referred to as FPGAs).

Next, the content of a process by the control section 17a of the transmission device 17 will be described.

FIG. 4 is a flowchart showing an example of the content of the process by the control section 17a of the transmission device 17.

Parallel input data from the ADC 16 is stored into a register not shown. The input data is, for example, 16-bit image data. Here, image data of an endoscopic image is transmitted as transmitted data in units of 16 bits. The control section 17a reads the input data from the register (S1) and calculates DC balance (S2).

In the DC balance calculation, a DC balance value is determined by subtracting the number of bits having "1" as a second value from the number of bits having "0" as a first value in input data of a predetermined number of bits, for example, 16 bits. For example, if the number of bits having the value of "0" is 6, and the number of bits having the value of "1" is 10, then the DC balance value is "−4". The sign of the DC balance value "−4" is "−" (minus). For example, if the number of bits having the value of "0" is 11, and the number of bits having the value of "1" is 5, then the DC balance value is "6", and the sign of the DC balance "6" is "+" (plus).

The process of S2 constitutes a subtraction section for calculating a subtraction value obtained by subtracting the number of bits having a second value from the number of bits having a first value in input data constituted by a collection of a predetermined number of bits each of which has the first or the second value.

The control section 17a compares the sign of the DC balance value of the input data and the sign of a cumulative value of the cumulative DC balance value in the past and judges whether the sign of the DC balance value of the input data is the same as the sign of the cumulative value (S3).

For example, if the sign of the cumulative value is minus, and the sign of input data is also minus, then the signs are judged to be the same sign.

When the sign of the cumulative value of the DC balance value and the sign of the DC balance value of the input data are the same sign (S3: YES), the control section 17a inverts all the bits of the input data to generate intermediate data (S4). Then, the control section 17a generates inversion information indicating that all the bits of the input data have been inverted, as predetermined information (S5). When the sign of the cumulative value of the DC balance value and the sign of the DC balance value of the input data are not the same sign (S3: NO), the input data is set as intermediate data (S9).

The process of performing the processes of S3, S4, S5 and S9 for input data to generate intermediate data constituted by a predetermined number of bits constitutes a data processing section.

When the sign of the cumulative value of the DC balance value and the sign of the DC balance value of the input data are not the same sign (S3: NO), and after all the bits are inverted, the control section 17a calculates the DC balance of the intermediate data (S6). The control section 17a calculates the DC balance of the intermediate data generated at S4. Otherwise, in the case of NO at S3, the control section 17a sets the input data as intermediate data and calculates the DC balance thereof. That is, the control section 17a calculates a subtraction value obtained by subtracting the number of bits having the second value from the number of bits having the first value in the intermediate data.

The process of S6 constitutes a subtraction section for calculating a subtraction value obtained by subtracting the number of bits having the second value from the number of bits having the first value in the intermediate data.

That is, the control section 17a performs a predetermined process for input data to generate intermediate data constituted by a predetermined number of bits. Then, as the predetermined process, the control section 17a performs a process of: comparing the sign of the subtraction value obtained for the input data and the sign of the cumulative value described above; generating the intermediate data by exchanging the first value and the second value with each other for all the bits of the input data and generating predetermined information indicating inversion of all the bits when the sign of the subtraction value and the sign of the cumulative value are the same sign; and setting the input data as intermediate data when the sign of the subtraction value and the sign of the cumulative value are different signs.

Then, the control section 17a updates the cumulative value to a latest value by adding the DC balance value of the intermediate data (the input data the bits of which have been inverted or the input data the bits of which have not been inverted) to a cumulative value in the past (S7). That is, the control section 17a executes an accumulation process for calculating a cumulative value of the calculated subtraction value. The process of S7 constitutes an accumulation section for calculating a cumulative value of the subtraction value.

Then, the control section 17a transmits the intermediate data by a serial signal (S8). In the case where the inversion information is generated, the control section 17a also transmits the inversion information. The process of S8 constitutes a transmission section for transmitting the intermediate data by a serial signal.

For example, if the intermediate data is constituted by 16 bits, the inversion information requires only addition of 1 bit. Therefore, the amount of communication between the transmission device 17 and the reception device 19 does not increase much for the number of bits of input data.

In the case where the input data is image information, the control section 17a performs control to include inversion information about each input data during a so-called blanking period in a video signal so that the inversion information is collectively transmitted. To transmit inversion information during a blanking period in a video signal as described above is advantageous in that it is unnecessary to add a bit for each unit of 16 bits of input data.

Next, the content of a process by the control section 19a of the reception device 19 will be described.

Figure 5:
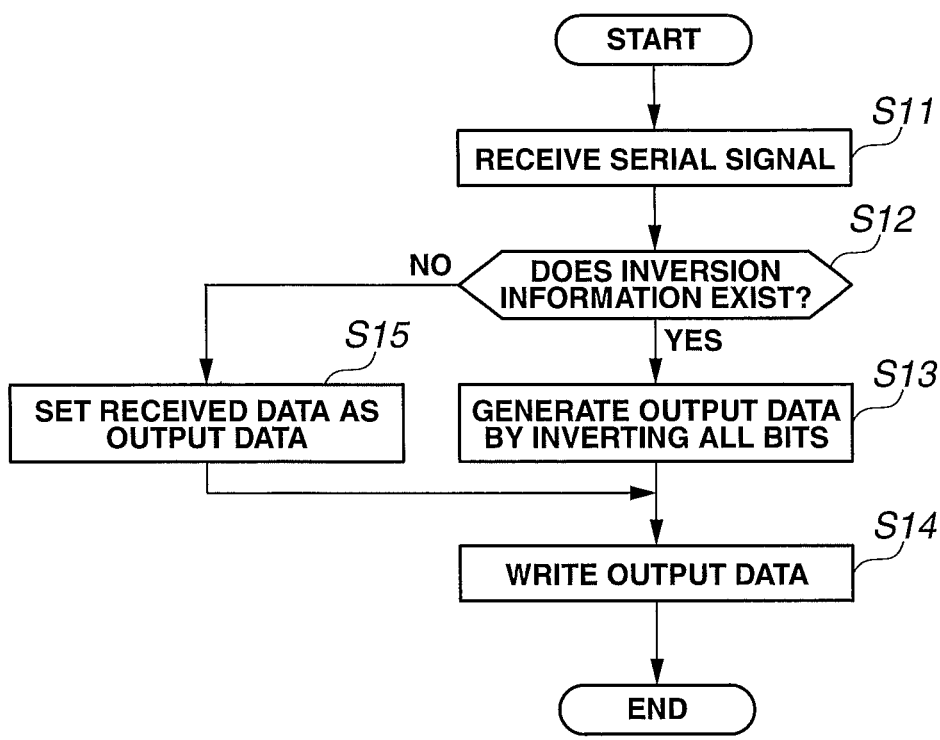
FIG. 5 is a flowchart showing an example of the content of a process by a control section 19a of the reception device 19 according to the first embodiment of the present invention.

FIG. 5 is a flowchart showing an example of the content of the process by the control section 19a of the reception device 19.

The serial signal transmitted via the cable 13 is received by the control section 19a via the insulating portion 18 (S11). The process of S11 constitutes a serial reception section for receiving a serial signal and outputting the serial signals as received data for each predetermined number of bits.

The control section 19a judges whether there is inversion information about the received data which have been received (S12), and, if the inversion information is included (S12: YES), inverts all the bits of the received data (S13). If the inversion information is not included (S12: NO), inversion of the received data is not performed, and the received data is set as output data (S15). The process of performing the processes of S12, S13 and S15 for received data to generate output data constituted by a predetermined number of bits constitutes a data processing section.

As described above, in the case of receiving image information, the control section 19a judges whether inversion information about each received data exists or not, on the basis of inversion information received during a blanking period in a video signal.

If the inversion information does not exist (S12: NO), the control section 19a writes the received data into a predetermined register or memory as output data (S14). If the inversion information exists (S12: YES), the control section 19a inverts all the bits of the received data and writes the data into the predetermined register or memory as output data (S14).

That is, the control section 19a performs a predetermined process for received data obtained by deserializing a serial signal to generate output data constituted by a predetermined number of bits. Especially, as the predetermined process, the control section 19a generates output data by exchanging the first value and the second value with each other for all the bits of received data when predetermined information is generated, and sets the received data as the output data when the predetermined information is not generated.

As described above, according to the transmission device 17 and the reception device 19 according to the embodiment described above, the transmission device 17 judges whether the sign of the DC balance value of input data and the sign of a cumulative DC balance value are the same or not, inverts the input data on the basis of a result of the judgment, and transmits the input data to the reception device 19 by a serial signal. Then, inversion information indicating that the input data has been inverted is added to the inverted input data or separately generated, and transmitted to the reception device 19.

The reception device 19 judges whether the received data obtained by deserializing the serial signal is inverted or not, on the basis of the received inversion information. If the inversion information is added to the received data or generated, the received data which has been received is inverted, and the same output data as the input data inputted to the transmission device 17 is outputted.

Thus, according to the transmission device 17 and the reception device 19 described above, much increase in the number of bits of input data does not accompany, and, therefore, it is possible to perform communication for which DC balance is ensured without increasing the transmission rate. Since there is a great demand for reduction of the diameter of the insertion portion of an endoscope, it is not possible to thicken signal lines, and, therefore, it is difficult to increase the transmission rate. According to the present embodiment, it is possible to perform communication without increasing the transmission rate.

Note that, as a variation of the present embodiment, the cumulative value of the DC balance value may be initialized in a predetermined cycle because there is a possibility that the cumulative value of the DC balance value may be calculated with error data due to communication errors and the like included.

Figure 6:
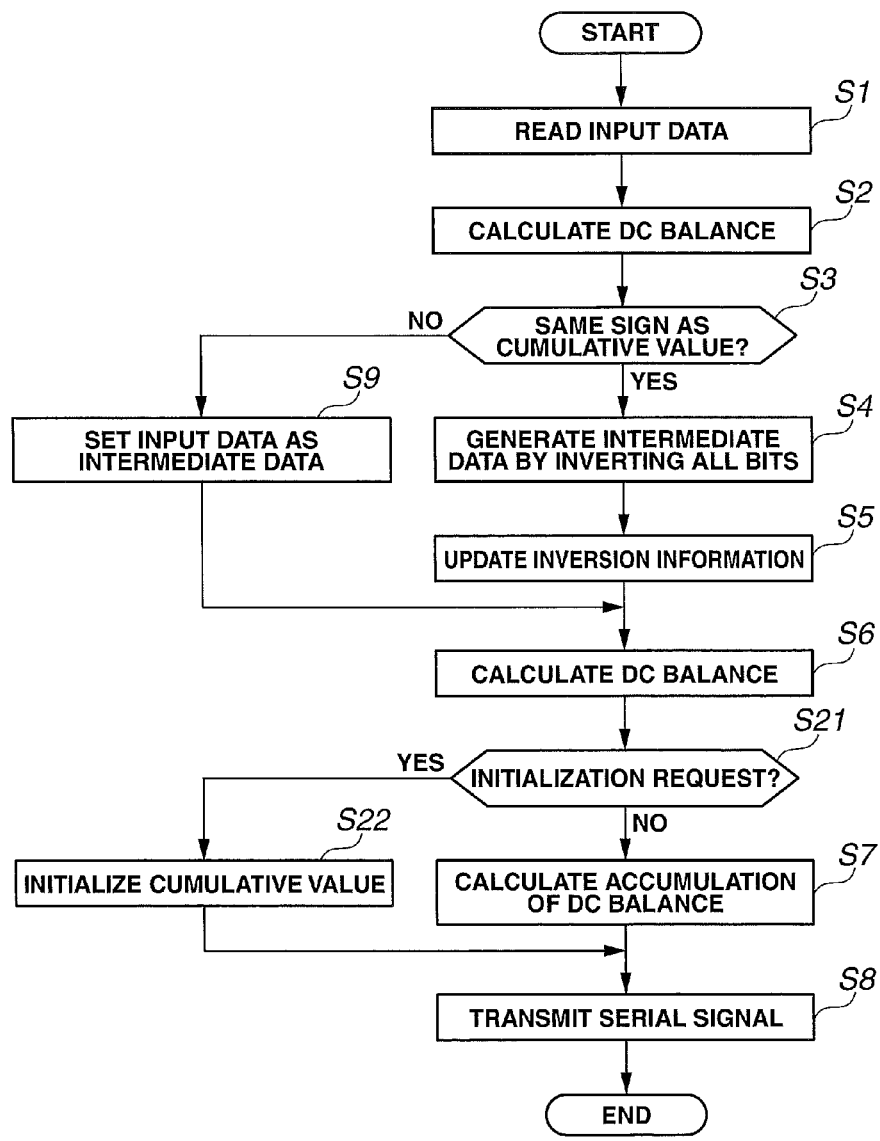
FIG. 6 is a flowchart showing an example of the content of a process by the control section 17a of the transmission device 17 in the case where a cumulative value initialization process is included, according to the first embodiment of the present invention.

FIG. 6 is a flowchart showing an example of the content of a process by each control section of the transmission device 17 in the case where a cumulative value initialization process is included. The same processes as in FIG. 4 are given the same reference numerals, and description thereof will be omitted. In FIG. 6, after S6, it is judged whether an initialization request has been received or not (S21). If the initialization request has been received (S21: YES), a cumulative value is initialized (S22).

As for the initialization request in the case where input data is image information, for example, a signal such as a horizontal synchronizing signal and a vertical synchronizing signal may be a signal indicating existence or nonexistence of the initialization request.

Otherwise, a timer circuit for counting a predetermined time period may be provided so that a timeout signal in a predetermined cycle outputted by the timer circuit may be a signal indicating existence or nonexistence of the initialization request. Thus, the process of S22 constitutes an initialization section for initializing the cumulative value of the accumulation section in a predetermined cycle.

By adding such an initialization process, it is possible to eliminate errors of the cumulative value and perform correct DC balance adjustment.

Note that, though the process described above is realized by a software program at the control sections 17a and 19a of the transmission device 17 and the reception device 19, the process may be realized by a hardware circuit.

Figure 7:
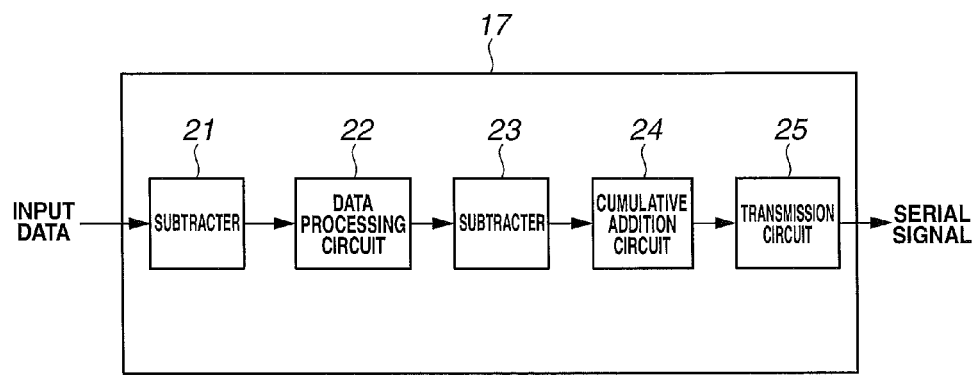
FIG. 7 is a block diagram showing a configuration of a hardware circuit of the transmission device 17 according to the first embodiment of the present invention.

FIG. 7 is a block diagram showing a configuration of the hardware circuit of the transmission device 17 in that case. The transmission device 17 is configured such that it includes a subtracter 21, a data processing circuit 22, a subtracter 23, a cumulative addition circuit 24 and a transmission circuit 25. The subtracter 21 is a circuit for inputting input data to calculate DC balance. The subtracter 21 calculates DC balance, which is a subtraction value, by subtracting the number of bits of "1" as a second value from the number of bits of "0" as a first value in input data constituted by a predetermined number of bits.

In FIG. 7, the subtracter 21 constitutes a first subtraction section for calculating a first subtraction value obtained by subtracting the number of bits having a second value from the number of bits having a first value in input data constituted by a collection of a predetermined number of bits each of which has the first or the second value.

The data processing circuit 22 constitutes a first data processing section for performing a first predetermined process for the input data to generate intermediate data constituted by the predetermined number of bits.

The subtracter 23 constitutes a second subtraction section for calculating a second subtraction value obtained by subtracting the number of bits having the second value from the number of bits having the first value in the intermediate data.

The cumulative addition circuit 24 constitutes a first accumulation section for calculating a cumulative value of the second subtraction value.

The transmission circuit 25 constitutes a transmission section for transmitting the intermediate data by a serial signal.

Note that, in the DC balance calculation, the number of bits having the value of "0" as a second value may be subtracted from the number of bits having the value of "1" as a first value. That is, the subtracter 21 is a circuit for calculating a subtraction value obtained by subtracting the number of bits having a second value from the number of bits having a first value in input data constituted by a collection of a predetermined number of bits each of which has the first or the second value.

The data processing circuit 22 compares a sign obtained as a result of the DC balance calculation and the sign of the cumulative value, performs a necessary bit inversion process for the input data to generate intermediate data, and performs a process of generating predetermined information indicating inversion of all the bits.

The subtracter 23 is a circuit for calculating the DC balance of the bit-inverted data.

The cumulative addition circuit 24 is a circuit for adding the DC balance value of the intermediate data (bit-inverted input data or bit-uninverted input data) to a cumulative value in the past to calculate a cumulative value of DC balance.

The transmission circuit 25 is a circuit for transmitting the intermediate data via the signal lines 13a of the cable 13 by a serial signal.

Figure 8:
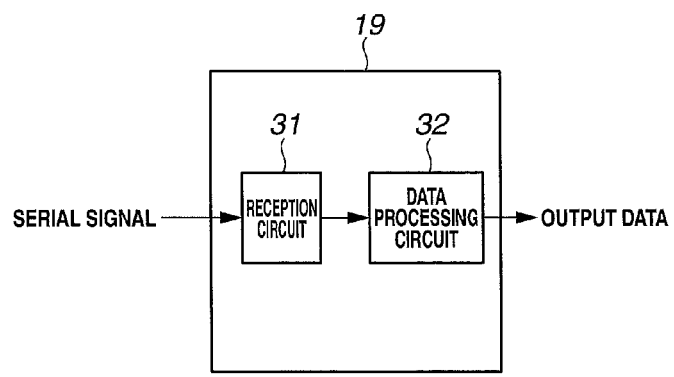
FIG. 8 is a block diagram showing a configuration of a hardware circuit of the reception device 19 according to the first embodiment of the present invention.

FIG. 8 is a block diagram showing a configuration of a hardware circuit of the reception device 19. The reception device 19 is configured such that it includes a reception circuit 31 and a data processing circuit 32. The reception circuit 31 is a circuit for receiving a serial signal of intermediate data from the transmission device 17 and outputs the serial signals as received data for each predetermined number of bits.

The reception circuit 31 constitutes a serial reception section for receiving a serial signal and outputting the serial signals as received data for each predetermined number of bits.

The data processing circuit 32 constitutes a second data processing section for performing a second predetermined process for received data to generate output data constituted by a predetermined number of bits.

The data processing circuit 32 is a circuit for performing a necessary bit inversion process to generate output data on the basis of predetermined information, as described above.

As described above, the content of the processes shown in FIGS. 4 and 5 may be realized by circuits as shown in FIGS. 7 and 8.

Second Embodiment

In the first embodiment, the transmission device 17 compares the sign of the DC balance value of input data and the sign of a cumulative value of the DC balance value and performs inversion of the input data. In a second embodiment, furthermore, a reception device is provided with a function of judging whether the DC balance of received data to be received is correctly adjusted or not.

A transmission device of the present embodiment is configured the same as the transmission device 17 of the first embodiment. Therefore, description thereof will be omitted, and description will be made mainly on a reception device. Though the configuration of a reception device 19A of the present embodiment is similar to the configuration shown in FIG. 3, the content of a process by the reception device 19A is different. Therefore, the different content of the process will be described.

FIG. 9 is a flowchart showing an example of the content of the process by a control section 19a of the reception device 19A. In FIG. 9, the same processes as the processes in FIG. 5 are given the same reference numerals, and description thereof will be simplified.

A serial signal of intermediate data transmitted via a cable 13 is received by the control section 19a via an insulating portion 18 (S11). The control section 19a calculates the DC balance of the received data which has been received (S31). The process of S31 constitutes a subtraction section for calculating a subtraction value obtained by subtracting the number of bits having a second value from the number of bits having a first value in the received data.

The control section 19a compares the sign of the DC balance value of the received data which has been received and the sign of a cumulative value of the cumulative DC balance value in the past and judges whether the sign of the DC balance value of the received data is the same as the sign of the cumulative value (S32). The cumulative value is a cumulative value of the DC balance value of the received data which has been received. The process of S32 constitutes an accumulation section for calculating a cumulative value of the subtraction value.

When the sign of the cumulative value of the DC balance value and the sign of the DC balance value of the received data are the same sign (S32: YES), the control section 19a generates and transmits error information (S33). That is, the control section 19a compares the sign of a subtraction value of the received data and the sign of the cumulative value, and, when the sign of the subtraction value and the sign of the cumulative value are the same sign, generates and outputs predetermined error information. The process of S33 constitutes an abnormality detection section for comparing the sign of the subtraction value of received data and the sign of a cumulative value of the accumulation section, and, when the sign of the subtraction value and the sign of the cumulative value are the same sign, generating predetermined error information.

When the sign of the cumulative value of the DC balance value and the sign of the DC balance value of the received data are not the same sign (S32: NO), the control section 19a adds the DC balance value of the received data to the cumulative value in the past to update the cumulative value to a latest cumulative value (S34).

After S34, the processes of S12, S13, S14 and S15 are executed.

As described above, according to the transmission device 17 and the reception device 19A of the present embodiment, it is possible to perform communication for which DC balance is ensured without being accompanied by much increase in the number of bits of input data, and it is also possible to detect DC balance adjustment and communication abnormalities at the reception device 19A in real time without being accompanied by much increase in the number of input bits.

Note that, at the reception device 19A also, the cumulative value of the DC balance value may be initialized in a predetermined cycle because there is a possibility that the cumulative value of the DC balance value may be calculated with error data due to communication errors and the like included, similarly to the variation of the first embodiment.

The reception device 19A of the present embodiment can be also realized by a hardware circuit. FIG. 10 is a block diagram showing a configuration of the hardware circuit of the reception device 19A in that case. The reception device 19A is configured such that it includes a reception circuit 31, a subtracter 41, an abnormality detection circuit 42, a cumulative addition circuit 43 and a data processing circuit 32. In FIG. 10, the same components as in FIG. 8 are given the same reference numerals, and description thereof will be omitted. Note that a transmission device and a reception device in the present embodiment are also circuit devices realized by FPGAs.

That is, the subtracter 41 constitutes a third subtraction section for calculating a third subtraction value obtained by subtracting the number of bits having a second value from the number of bits having a first value in received data.

The cumulative addition circuit 43 constitutes a second accumulation section for calculating a cumulative value of the third subtraction value.

The abnormality detection circuit 42 constitutes an abnormality detection section for comparing the sign of the third subtraction value of received data and the sign of a cumulative value of the second accumulation section, and, when the sign of the third subtraction value and the sign of the cumulative value of the second accumulation section are the same sign, generating predetermined error information.

The subtracter 41 is a circuit which has the same functions as the subtracter 21 and is for inputting received data to calculate DC balance. That is, the subtracter 41 calculates a subtraction value obtained by subtracting the number of bits having a second value from the number of bits having a first value in the received data.

The abnormality detection circuit 42 is a circuit for detecting whether DC balance adjustment is normal or not from a DC balance value calculated by the subtracter 41 as described later.

The cumulative addition circuit 43 is a circuit which has the same functions as the cumulative addition circuit 24 and is for calculating a cumulative value of DC balance by adding the DC balance value of received data which has been received to a cumulative value in the past. That is, the cumulative addition circuit 43 calculates a cumulative value of the subtraction value of the subtracter 41.

As described above, the content of the process shown in FIG. 9 may be realized by a circuit as shown in FIG. 10.

The various cables 13 used for the endoscope apparatus 1 are generally designed and manufactured so that they are provided with sufficient mechanical resistance in consideration of various use states. However, when the cables are used beyond the scope of assumption, there is a possibility that the cables are broken, but, conventionally, the cables are not provided with means for predicting such breakage.

Therefore, the means for predicting breakage of a cable constituted by multiple cables which makes connection between devices or between boards will be described. Here, description will be made with the multiple signal lines 13a in the cable 13 as an example.

Figure 11:
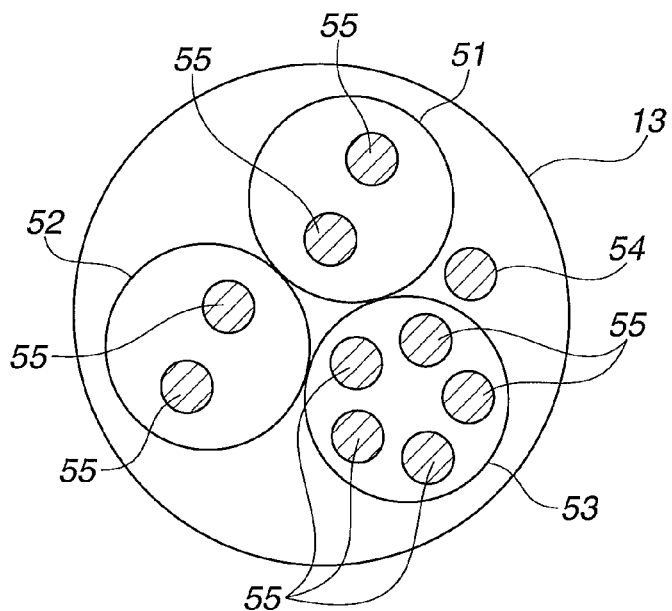
FIG. 11 is a cross-sectional view of a cable 13.

FIG. 11 is a cross-sectional view of the cable 13. The cable 13 is configured such that it includes a cable 51 for a driving signal which drives the image pickup device 14a provided at the distal end portion of the endoscope 11, a cable 52 for an image signal from the image pickup device 14a, a cable 53 for an operation signal related to the operation section 15, and a detection line 54 for detection of breakage. The detection line 54 is a conductor wire thinner than the cables 51, 52 and 53.

Each of the cables 51, 52 and 53 is constituted by multiple conductor wires 55 twisted together. The multiple conductor wires 55 correspond to the multiple signal lines 13a described above. The cable 13 is configured by the three cables 51, 52 and 53 and the one detection line 54 being twisted together. Therefore, the cable 13 has a high bending resistance due to the double twists.

If the cable 13 having such a configuration is used beyond the scope of assumption, the detection line 54 is damaged earlier than the conductor wires 55 in the cables 51, 52 and 53 because the detection line 54 is thinner and has a strength lower than the strength of the cables 51, 52 and 53.

Therefore, by detecting the voltage or current of the detection line 54, breakage of the conductor wires 55 in the cables 51, 52 and 53 responsible for main functions of the endoscope apparatus can be predicted. For example, if it is detected that the voltage or current of the detection line 54 is above or below a predetermined voltage or current, a detection signal for the detection is transmitted to the processor 12, and a message or the like to the effect that there is a possibility of breakage of the cable 13 is displayed on a monitor (not shown) connected to the processor 12 so that a user is notified thereof.

Note that, though description has been made on the example of the cable 13 which includes three cables here, the number of cables targeted by prediction by the breakage prediction means is not limited to three.

Furthermore, it is also possible to, when the cable 13 includes multiple cables, detect which cable may be possibly broken.

Figure 12:
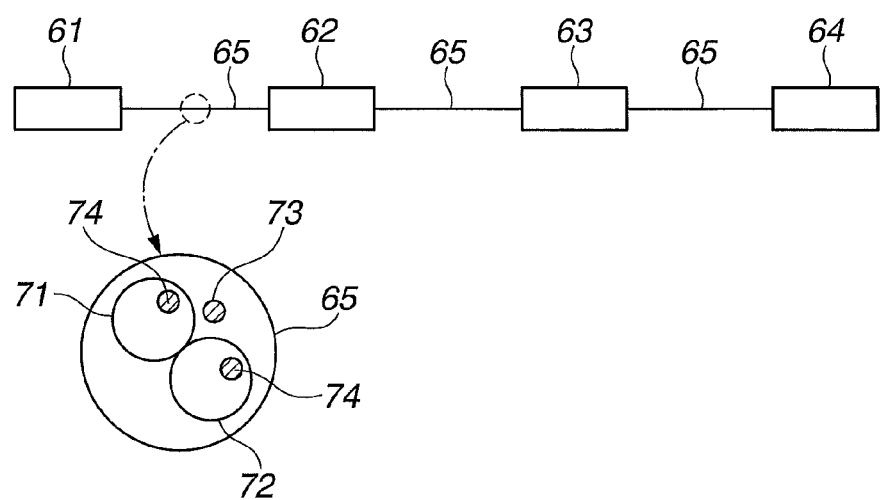
FIG. 12 is a diagram for illustrating a configuration example making it possible to, when multiple cables are connected in series, identify a cable which may be broken.

FIG. 12 is a diagram for illustrating a configuration example making it possible to, when multiple cables are connected in series, identify a cable which may be possibly broken. As shown in FIG. 12, four circuit boards 61, 62, 63 and 64 are connected via three cables 65. The circuit boards 61 and 62, the circuit boards 62 and 63, the circuit boards 63 and 64 are connected via the cables 65, respectively.

Each cable 65 is a signal line having the same structure. Each cable 65 is configured such that it includes cables 71 and 72, and a detection line 73 for detection of breakage. The cables 71 and 72 are covered cables each of which includes a conductor wire 74, and the detection line 73 is a conductor wire thinner than the cables 71 and 72.

Each cable 65 in FIG. 12 is configured by the two cables 71 and 72 and the one detection line 73 which are twisted together. Furthermore, each of the cables 71 and 72 is constituted by multiple conductor wires 74 twisted together. Therefore, each of the cables 65 has a high bending resistance due to the double twists.

Thus, two circuit boards are connected via a signal line, and the detection line 73 is included in the signal line. Therefore, if the cable 65 is used beyond the scope of assumption, the detection line 73 in the cable 65 is damaged earlier than the conductor wires 74 in the cables 71 and 72.

Therefore, by detecting the voltage or current of the detection line 74, breakage of the other cables 71 and 72 can be predicted. For example, if breakage of the detection line 73 between the circuit boards 61 and 62 is detected, prediction of breakage of the cable 65 between the circuit boards 61 and 62 can be judged.

By connecting such multiple circuit boards in series via such cables as described above, it is also possible to detect which cable may be possibly broken. Since breakage can be predicted, it becomes possible, for example, to shorten an unusable period of the endoscope apparatus to be of the minimum length, and an advantage can be obtained that breakage examination of the endoscope apparatus can be simplified and realized at a low cost.

As described above, according to the communication device according to the embodiment described above, the transmission device judges whether the sign of the DC balance value of input data and the sign of a cumulative DC balance value are the same or not, inverts the input data on the basis of a result of the judgment, and transmits the input data to the reception device. Then, the inverted input data is transmitted to the reception device with inversion information indicating that the input data has been inverted added thereto or separately generated. Thus, according to the embodiment described above, it is possible to provide a communication device capable of performing communication for which DC balance is ensured, without being accompanied by much increase in the number of bits of input data, an endoscope apparatus and a communication method.

The present invention is not limited to the embodiments described above, and various modifications, alterations and the like are possible within a range not departing from the spirit of the present invention.

What is claimed is:

1. An endoscope apparatus comprising an endoscope including an image pickup device and a transmission device, and a processor including a reception device communicating with the transmission device, wherein
the transmission device of the endoscope comprises:
a first subtraction section calculating a first subtraction value obtained by subtracting a number of bits having a second value from a number of bits having a first value in input data constituted by a collection of a predetermined number of bits each of which has the first or the second value, the input data being image data of a video signal from the image pickup device;
a first data processing section performing a first predetermined process for the input data to generate intermediate data constituted by the predetermined number of bits;
a second subtraction section calculating a second subtraction value obtained by subtracting the number of bits having the second value from the number of bits having the first value in the intermediate data;
a first accumulation section calculating a cumulative value of the second subtraction value; and
a transmission section transmitting the intermediate data by a serial signal; wherein
the first predetermined process is a process of: comparing a sign of the first subtraction value of the input data and a sign of the cumulative value of the first accumulation section; generating the intermediate data by exchanging the first value and the second value with each other for all the bits of the input data and generating predetermined information indicating inversion of all the bits when the sign of the first subtraction value and the sign of the cumulative value are the same sign; and setting the input data as the intermediate data when the sign of the first subtraction value and the sign of the cumulative value are different signs;
the transmission section causes the predetermined information of each input data to be included in a blanking period in the video signal so that the predetermined information is collectively transmitted; and
the reception device of the processor comprises:
a serial reception section receiving the serial signal and outputting the serial signal as received data for each predetermined number of bits;
a second data processing section generating, for the received data, output data by exchanging the first value and the second value with each other for all the bits of the received data when the predetermined information is generated, and generating the received data which is received as the output data when the predetermined information is not generated;
a third subtraction section calculating a third subtraction value obtained by subtracting the number of bits having the second value from the number of bits having the first value in the received data;
a second accumulation section calculating a cumulative value of the third subtraction value; and
an abnormality detection section comparing a sign of the third subtraction value of the received data and a sign of the cumulative value of the second accumulation section, and, when the sign of the third subtraction value and the sign of the cumulative value of the second accumulation section are the same sign, generating predetermined error information.

2. The endoscope apparatus according to claim 1, wherein the first accumulation section and the second accumulation section initialize the cumulative value in a predetermined cycle.

3. The endoscope apparatus according to claim 2, wherein the predetermined cycle is a cycle of a horizontal synchronizing signal or a vertical synchronizing signal of the video signal.

4. An endoscope apparatus comprising an endoscope including an image pickup device and a transmission device, and a processor including a reception device communicating with the transmission device, wherein the transmission device of the endoscope comprises:
a first subtraction section calculating a first subtraction value obtained by subtracting a number of bits having a second value from a number of bits having a first value in input data constituted by a collection of a predetermined number of bits each of which has the first or the second value, the input data being image data of a video signal from the image pickup device;
a first data processing section performing a first predetermined process for the input data to generate intermediate data constituted by the predetermined number of bits;
a second subtraction section calculating a second subtraction value obtained by subtracting the number of bits having the second value from the number of bits having the first value in the intermediate data;
a first accumulation section calculating a cumulative value of the second subtraction value; and
a transmission section transmitting the intermediate data by a serial signal; wherein
the first predetermined process is a process of: comparing a sign of the first subtraction value of the input data and a sign of the cumulative value of the first accumulation section; generating the intermediate data by exchanging the first value and the second value with each other for all the bits of the input data and generating predetermined information indicating inversion of all the bits when the sign of the first subtraction value and the sign of the cumulative value are the same sign; and setting the input data as the intermediate data when the sign of the first subtraction value and the sign of the cumulative value are different signs;
the transmission section causes the predetermined information of each input data to be included in a blanking period in the video signal so that the predetermined information is collectively transmitted; and
the reception device of the processor comprises:
a serial reception section receiving the serial signal and outputting the serial signal as received data for each predetermined number of bits;
a second data processing section generating, for the received data, output data by exchanging the first value and the second value with each other for all the bits of the received data when the predetermined information is generated, and generating the received data which is received as the output data when the predetermined information is not generated;
a third subtraction section calculating a third subtraction value obtained by subtracting the number of bits having the second value from the number of bits having the first value in the received data; and
a second accumulation section calculating a cumulative value of the third subtraction value.

* * * * *